United States Patent
Ii et al.

(10) Patent No.: US 9,656,942 B2
(45) Date of Patent: May 23, 2017

(54) METHOD OF MANUFACTURING DIETHYL CARBONATE

(71) Applicant: Ube Industries, Ltd., Ube (JP)

(72) Inventors: Hirofumi Ii, Ube (JP); Tatsuya Naitou, Ube (JP); Kazuki Yamamoto, Ube (JP); Katsuyoshi Kudou, Ube (JP); Akira Hino, Ube (JP); Tadaaki Kaneko, Ube (JP); Takamasa Miyazaki, Ube (JP); Tomoyuki Itou, Ube (JP)

(73) Assignee: Ube Industries, Ltd. (JP)

( * ) Notice: Subject to any disclaimer, the term of this patent is extended or adjusted under 35 U.S.C. 154(b) by 149 days.

(21) Appl. No.: 14/434,153

(22) PCT Filed: Oct. 15, 2013

(86) PCT No.: PCT/JP2013/078012
§ 371 (c)(1),
(2) Date: Apr. 8, 2015

(87) PCT Pub. No.: WO2014/061678
PCT Pub. Date: Apr. 24, 2014

(65) Prior Publication Data
US 2015/0291504 A1    Oct. 15, 2015

(30) Foreign Application Priority Data

Oct. 15, 2012  (JP) ................................. 2012-228457

(51) Int. Cl.
C07C 68/06 (2006.01)
C07C 68/08 (2006.01)
C07C 69/56 (2006.01)

(52) U.S. Cl.
CPC ............ *C07C 68/065* (2013.01); *C07C 68/06* (2013.01); *C07C 68/08* (2013.01)

(58) Field of Classification Search
CPC .......... C07C 68/06; C07C 68/08; C07C 69/96
See application file for complete search history.

(56) References Cited

U.S. PATENT DOCUMENTS

| 5,455,368 A | 10/1995 | Janisch et al. |
| 8,049,028 B2 * | 11/2011 | Fukuoka ............ B01D 3/009 558/277 |
| 2011/0313185 A1 | 12/2011 | Shimizu |

FOREIGN PATENT DOCUMENTS

| JP | 3-141243 | 6/1991 |
| JP | 7-196584 | 8/1995 |
| JP | 2006-176412 | 7/2006 |
| JP | 2010-168365 | 8/2010 |
| WO | 2007/096343 | 8/2007 |

OTHER PUBLICATIONS

F.M. Mei, et al., "Effective and Recoverable Homogeneous Catalysts for the Transesterification of Dimethyl Carbonate with Ethanol: Lanthanide Triflates", *Kinetics and Catalysis*, 2009, vol. 50, No. 5, p. 666-670.
H.-Y. Wei, et al., "Design and control of reactive-distillation process for the production of diethyl carbonate via two consecutive transesterification reactions", *Journal of Process Control*, 2011, vol. 21, No. 8, p. 1193-1207.
T. Keller, et al., "Transesterification of dimethyl carbonate with ethanol in a pilot-scale reactive distillation column", *Chemical Engineering Journal*, Jan. 2012, vol. 180, p. 309-322.
I. Mueller, et al., "Reactive Distillation in a Dividing Wall Column: Rate-Based Modeling and Simulation", *Industrial & Engineering Chemistry Research*, 2007, vol. 46, p. 3709-3719.

* cited by examiner

*Primary Examiner* — Sun Jae Yoo
(74) *Attorney, Agent, or Firm* — DLA Piper LLP (US)

(57) ABSTRACT

A method manufactures diethyl carbonate by reaction distillation where transesterification and distillation are simultaneously performed in a multistage reaction distillation column provided with a catalyst introduction port and a raw material introduction port located below the catalyst introduction port, wherein: (a) the reaction is performed in a countercurrent flow format in which contact is brought about between a transesterification catalyst, dimethyl carbonate, and ethanol; (e) 1 to 250 mmol of catalyst is used per mole of dimethyl carbonate; (f) the ratio of the volume of air in the catalyst introduction port and the raw material introduction port regarding the volume of air in the reaction distillation part is 0.1 to 0.9; (g) the recirculation ratio in the reaction distillation column is 0.5 to 10; and (h) the temperature of the top part of the column and the reaction distillation part is 60 to 100° C.

17 Claims, 2 Drawing Sheets

METHOD OF MANUFACTURING DIETHYL CARBONATE

TECHNICAL FIELD

The present invention relates to a method for producing diethyl carbonate at a high yield by reacting dimethyl carbonate with ethanol at a high reaction conversion rate in the presence of a transesterification catalyst.

More particularly, the present invention relates to a method for industrially producing a large amount of diethyl carbonate while separating the objective substance from by-products by continuous reactive distillation using a reactive distillation column.

BACKGROUND ART

In general, transesterification between a cyclic carbonate and ethanol is widely known as a method for producing diethyl carbonate (see, for example, Patent Literature 1 and Patent Literature 2).

For example, Patent Literature 1 describes a method in which, using propylene carbonate as a cyclic carbonate, a mixture of propylene glycol as a reaction by-product with dimethyl carbonate as the objective substance is obtained, and then the obtained mixture is separated by further distillation to obtain dimethyl carbonate. Patent Literature 2 describes a method in which, using ethylene carbonate as a cyclic carbonate, ethylene carbonate is transesterified with two or more types of alcohols in the same reactor to produce a symmetrical dialkyl carbonate and an asymmetrical dialkyl carbonate. Patent Literature 2 describes a method in which, after the reaction, a low-boiling fraction containing, as main components, a symmetrical dialkyl carbonate and an asymmetrical dialkyl carbonate as objective substances, and alcohol as a raw material for production is separated from a high-boiling fraction containing, as main components, an alkylene carbonate as a raw material for production and an alkylene glycol as a reaction by-product by distillation. This literature describes that purification additionally includes a means for extraction separation, since various alkyl glycol ethers, such as ethyl glycol ether to be by-produced during the reaction, are mixed in the low-boiling component, in addition to the objective symmetrical dialkyl carbonate and asymmetrical dialkyl carbonate, and also these alkyl glycol ethers cannot easily separated by distillation because of having an azeotropic relationship with the objective alkyl carbonate.

Several methods for industrially producing diethyl carbonate by transesterification using dimethyl carbonate (DMC) as a raw material for production have been reported (see, for example, Non Patent Literature 1).

For example, Non Patent Literature 1 describes using, as a transesterification catalyst, Lewis acid compounds, such as yttrium triflate and samarium triflate, dimethyl carbonate is reacted with ethanol to synthesize diethyl carbonate.

Most methods for producing diethyl carbonate using a cyclic carbonate or dimethyl carbonate (DMC) as raw materials for production comprise transesterification utilizing chemical equilibrium reaction. In order to allow this reaction to proceed efficiently, a method for distilling an alkylene glycol and methanol as reaction by-products is carried out. However, for example, since DMC forms an azeotropic mixture having the general composition of 70% methanol and 30% DMC with methanol under atmospheric pressure, and complete reaction of DMC is substantially impossible when this type of transesterification is carried out, DMC is distilled out of the reaction system together with methanol in an actual reaction, resulting in insufficient DMC conversion rate or low industrial reproducibility. Therefore, a further need for a method for separating and removing methanol from an azeotropic mixture of DMC with methanol is described (see, for example, Patent Literature 3).

CITATION LIST

Patent Literature

[Patent Literature 1]
  WO 2007/096343 A (Kohyo (National Publication of Translated Version) No. 2010-516729))
[Patent Literature 2]
  Kokai (Japanese Unexamined Patent Publication) No. 2010-168365
[Patent Literature 3]
  Kokai (Japanese Unexamined Patent Publication) No. 7-196584

Non Patent Literature

[Non Patent Literature 1]
Kinetics and Catalysis, 2009, Vol. 50, No. 5, pp. 666-670

SUMMARY OF THE INVENTION

Problems to be Solved by the Invention

As described in the above prior literatures, a method for producing diethyl carbonate using a reactive distillation column as in Patent Literature 1 is a common method for producing diethyl carbonate (DEC) using a cyclic carbonate; however, it was economically disadvantageous to separate diethyl carbonate having a boiling point of 127° C. from ethylene glycol (having a boiling point of 198° C.) or propylene glycol (having a boiling point of 188° C.) because of requiring complicated conditions, such as high distillation temperature and excess numbers of distillation stages. Furthermore, in a conventional method using a cyclic carbonate described in Patent Literature 2, after the reaction, the objective dialkyl carbonate, such as diethyl carbonate, was collectively obtained as a low-boiling component in the form of a mixture of the objective substance with alcohol as a raw material for production, alcohol as a by-product, and glycol ether as a by-products, which is likely to form an azeotropic compound with the objective substance. Therefore, it was frequently difficult to purify by separating from these by-products, or complicated operations for purification by separation were often required when high-purity diethyl carbonate is obtained thereafter.

It was hard to determine if the method described in Non Patent Literature 1 is an industrially suitable production method since the DEC selectivity is at most 87.2% (Table 5). According to this method, ethyl methyl carbonate (EMC) as a reaction intermediate is produced at a selectivity of 13.6%. Therefore, it was also a problem that separation of DEC as the objective substance from DMC as a raw material and EMC as a reaction intermediate, after completion of the reaction. Furthermore, even if a reaction catalyst is optimized, the DMC conversion rate is at most 91.6% (DEC selectivity is 80.7%, EMC selectivity is 16.2%, Table 1), and thus there is a need to use a large excess of ethanol so as to increase the yield of DEC. Therefore, this method was not satisfactory as an industrially producing method in view of economy, such as raw material cost.

It is well known that dimethyl carbonate forms an azeotropic mixture with methanol. Therefore, the method for producing diethyl carbonate by transesterification of dimethyl carbonate had a serious problem that when methanol as a by-product is distilled off, dimethyl carbonate as a raw material partially forms an azeotropic mixture with methanol to distill out of the reaction system with the progress of the reaction, resulting in low DMC conversion rate and low yield of DEC due to this distillation loss. In particular, in the case of producing by a reactive distillation method using a reactive distillation column, which is one of industrially efficient methods, variation factors, such as temperature and pressure variations in the reactive distillation column, exert a large influence on the degree of reaction progress and variation in gas-liquid composition in each distillation stage. Therefore, it was very difficult to establish a method for producing diethyl carbonate in which the reaction for increasing the yield of DEC as the objective substance is continuously carried out by converting DMC almost completely. As a result, most of conventional methods for producing diethyl carbonate were production methods associated with a difficulty in selective separation and obtainment of diethyl carbonate as the objective substance from a mixture after the reaction as a result of an insufficient conversion rate due to the above problem of the azeotropic mixture. In other words, the above problem of the azeotropic mixture becomes an obstacle, thus making it technically difficult to establish a method for continuously producing DEC enabling mass production, which has achieved an object of obtaining diethyl carbonate at a high yield by reacting dimethyl carbonate at a high conversion rate.

In light of the above problems, an object of the present invention is to provide an industrially suitable producing method in which diethyl carbonate is obtained at a high selectivity by reacting dimethyl carbonate with methanol at a high conversion rate without being distilled out of the reaction system as an azeotropic mixture, in the transesterification of dimethyl carbonate using ethanol. More specifically, an object of the present invention is to provide an industrially large-scale method for producing diethyl carbonate at a high yield, high selectivity, and high productivity in a stable manner over a long period of time, using a reactive distillation method in which dimethyl carbonate and ethanol each are continuously fed into a reactive distillation column at specific intervals to simultaneously carry out transesterification and distillation in the column in the presence of a transesterification catalyst. A further object of the present invention is to provide a method for designing a reactive distillation column suited for the above method for producing diethyl carbonate.

Means to Solve the Problems

The present invention includes the following embodiments [1] to [8].

[1] A method for producing diethyl carbonate by a reactive distillation method in which dimethyl carbonate and ethanol are continuously fed into a reactive distillation column to simultaneously carry out transesterification and distillation in the reactive distillation column in the presence of a transesterification catalyst, characterized in that:

(a) transesterification is in a countercurrent reaction mode in which a transesterification catalyst is brought into contact with dimethyl carbonate and ethanol;

(b) a reactive distillation column is a multistage reactive distillation column, having a column top part, a reaction distillation part having internals, and a concentrating part; and the side of the reaction distillation part is provided with a catalyst introduction port and a raw material introduction port located below the catalyst introduction port;

(c) the transesterification catalyst is fed through the catalyst introduction port;

(d) dimethyl carbonate and ethanol are fed through the raw material introduction port;

(e) the amount of the transesterification catalyst used for 1 mol of dimethyl carbonate is 1 to 250 mmol;

(f) the ratio of the spatial volume between the catalyst introduction port and the raw material introduction port to the spatial volume of the reaction distillation part is 0.1 to 0.9;

(g) the reflux ratio of the reactive distillation column is 0.5 to 10;

(h) the temperature in the column top part and the reaction distillation part is 60° C. to 100° C.

[2] The method for producing diethyl carbonate according to the above [1], wherein the internals are separated by perforated plate trays.

[3] The method for producing diethyl carbonate according to the above [2], wherein the number of stages of the reactive distillation column is 30 to 75.

[4] The method for producing diethyl carbonate according to the above [2] or [3], wherein the space between the raw material introduction port and the catalyst introduction port corresponds to 1 to 50 stages.

[5] The method for producing diethyl carbonate according to any one of the above [1] to [4], wherein in the reactive distillation column, the required number of reaction stages: $\Delta N$ defined as the number of stages between the catalyst introduction port and the raw material introduction port meets the following inequality expression (S):

$$\Delta N \geq \frac{v_0}{V_h} \times \frac{Conv}{3600 \times \exp(14.8311 - 5003.61/T) \times \frac{c}{B + rD} \times (1 - Conv)} \quad \text{Inequality Expression (S)}$$

where
$\Delta N$: Required number of reaction stages,
$v_0$: Total feed volume of dimethyl carbonate, ethanol, and transesterification catalyst to the reactive distillation column per unit time (L·h$^{-1}$),
$V_h$: Hold-up volume per reaction stage (L/number of stages),
Conv: Reaction conversion rate of dimethyl carbonate,
c: Feed amount of catalyst into reactive distillation column (mol·h$^{-1}$),
B: Extraction volume from bottom of reactive distillation column (L·h$^{-1}$),
r: Reflux ratio,
D: Extraction volume from top of reactive distillation column (L·h$^{-1}$), and
T: Column temperature (K).

[6] The method for producing diethyl carbonate according to the above [1], wherein in the reactive distillation column, the required reaction distance: $\Delta L$ defined as a distance between the catalyst introduction port and the raw material introduction port meets inequality expression (W):

Inequality Expression (W)

$$\Delta L \geq \frac{v_0}{d} \times \frac{Conv}{3600 \times \exp(14.8311 - 5003.61/T) \times \frac{c}{B+rD} \times (1-Conv)}$$

where
ΔL: Required reaction distance (m),
$v_0$: Total feed volume of dimethyl carbonate, ethanol, and transesterification catalyst to reactive distillation column per unit time ($L \cdot h^{-1}$),
d: Hold-up volume per meter in region between catalyst introduction port and raw material introduction port in reactive distillation column ($L \cdot m^{-1}$),
Conv: Reaction conversion rate of dimethyl carbonate,
c: Feed amount of catalyst into reactive distillation column ($mol \cdot h^{-1}$),
B: Extraction volume from bottom of reactive distillation column ($L \cdot h^{-1}$),
r: Reflux ratio,
D: Extraction volume from top of reactive distillation column ($L \cdot h^{-1}$), and
T: Column temperature (K).

[7] The method for producing diethyl carbonate according to any one of the above [1] to [6], wherein the pressure in the column top part and the concentrating part is normal pressure to 1,000 kPa.

[8] The Method for producing diethyl carbonate according to any one of the above [1] to [7], wherein the transesterification catalyst is at least one selected from the group consisting of an alkali metal hydroxide, an alkali metal carbonate compound, an alkali metal methoxide, and an alkali metal ethoxide.

Effects of the Invention

According to the production method of the present invention, by a reactive distillation method in which dimethyl carbonate and ethanol each are continuously fed into a reactive distillation column at specific intervals to simultaneously carry out the synthesis reaction and purification of diethyl carbonate in the column in the presence of a transesterification catalyst, for example, control of the feed position of a transesterification catalyst and the feed position of dimethyl carbonate and/or ethanol into the reactive distillation column, the use amount of a transesterification catalyst, the ratio of the use amount of dimethyl carbonate to that of ethanol, a column temperature, and the like can prevent an azeotropic mixture of dimethyl carbonate as a raw material for production and methanol from distilling out of the reactive distillation column to react dimethyl carbonate at a satisfactory reaction conversion rate, thus making it possible to obtain diethyl carbonate at satisfactory reaction selectivity. Particularly, according to the production method of the present invention, in a reactive distillation column including trays or packings, it is possible to optimize the required number of reaction stages or the required reaction distance defined as the space between the feed position of dimethyl carbonate and/or ethanol and the feed position of a transesterification catalyst, using a predetermined inequality expression, and to continuously produce diethyl carbonate in industrially large scale.

According to the production method of the present invention, since the objective substance of diethyl carbonate can be obtained as a high-boiling component, little influence of various by-products observed in the above Patent Literatures, Non Patent Literature, and the like is exerted. In other words, according to the production method of the present invention, it is possible to obtain high-purity diethyl carbonate by a very simple method.

Furthermore, it is possible to recycle a mixture of ethanol with methanol separated and recovered as a low-boiling component in the production method of the present invention as a raw material for producing diethyl carbonate again. In one embodiment of the present invention, the alkali metal compound used as the transesterification catalyst is inexpensive and easily available, and is used in a very small amount, unlike a resin-supported catalyst prepared by a special method as in Patent Literature 2; therefore, according to this embodiment, a producing method that is advantageous in view of economy (cost), produces few wastes, and places a reduced burden on environment can be provided.

MODE FOR CARRYING OUT THE INVENTION

The present invention will be described in detail below. One embodiment of the present invention relates to a method for continuously producing diethyl carbonate by transesterification of dimethyl carbonate with ethanol in a reactive distillation column.

<Production Method of the Present Invention>

Figure 1:
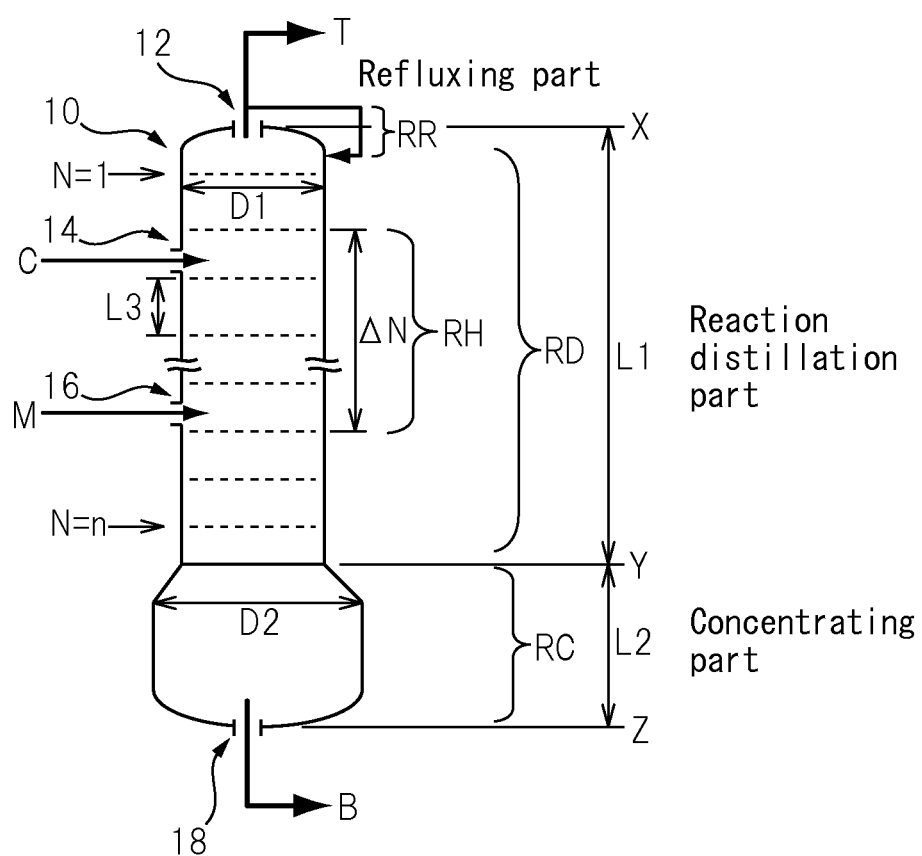
FIG. 1 is a schematic diagram showing the structure of a reactive distillation column according to one embodiment of the present invention.

The producing method of the present invention is a method for reacting dimethyl carbonate with ethanol in a reactive distillation column, which is exemplified in FIG. 1, in the presence of a transesterification catalyst. More specifically, the method comprises continuously feeding dimethyl carbonate and ethanol, which are raw materials for producing, and a transesterification catalyst into a reactive distillation column, simultaneously carrying out transesterification and a separation operation by distillation in the column, selectively and continuously separating by distillation a low-boiling compound with a boiling point of 80° C. or less including ethanol, which is a raw material for production (boiling point is 78.3° C.; atmospheric pressure), methanol that is produced by reaction (boiling point is 64.7° C.; atmospheric pressure), and the like from a column top part, and selectively separating diethyl carbonate, which is the objective substance, from a column bottom part to obtain.

The reaction in the present invention is a chemical equilibrium reaction by transesterification of dimethyl carbonate with ethanol. Therefore, the production method of the present invention can shift the reaction equilibrium toward the production of diethyl carbonate by continuously recovering methanol that is produced by reaction as a low-boiling compound from the column top, and as a result, can continuously produce the objective diethyl carbonate more efficiently. Since dimethyl carbonate, which is a raw material for production, is known to form an azeotropic mixture with methanol, in the production method of the present invention, for example, the structure of a reactive distillation column, reaction conditions in the reactive distillation column, and the like are designed to avoid distillation of this azeotropic mixture as a low-boiling component.
(Production Apparatus of the Present Invention)

The method for producing diethyl carbonate of the present invention is carried out by using, for example, a producing apparatus that enables continuous production, having a reactive distillation column having, for example, trays or packings as internals therein, as shown in FIG. 1.

For example, a reactive distillation column: 10 according to one embodiment of the present invention as shown in FIG. 1 has a refluxing part: RR, a reaction distillation part: RD, and a concentrating part: RC and the reaction distillation part: RD has internals. A column top part of the reactive distillation column: 10 is provided with a column top fraction recovery port: 12 and a column bottom part of it is provided with a column bottom fraction recovery port: 18, and the side of the reaction distillation part: RD is provided with a catalyst introduction port: 14 and a raw material introduction port: 16 located below the catalyst introduction port: 14. It may be further provided with the second raw material introduction port (figure not shown) located below the catalyst introduction port. Although FIG. 1 shows trays of N=1 to n as internals, the internals may be constituted of packings or a combination of trays and packings. The N related to the part of internals constituted of packings means the number of theoretical plates. The X, Y, and X in FIG. 1 represent a column top part, an upper column bottom, and a lower column bottom, respectively; D1 and D2 represent the inner diameter of the reaction distillation part and the concentrating part, respectively; L1 and L2 represent the length of the reaction distillation part and the concentrating part, respectively; L3 represents the space between trays.

(Internals in Distillation Column)

The reactive distillation column of the present invention is preferably a distillation column having trays and/or packings as internals. The internal referred in the present invention means a part in a distillation column that actually allows gas-liquid contact. Such trays are preferably, for example, a bubble tray, perforated plate tray, ripple tray, ballast tray, valve tray, countercurrent tray, uniflux tray, Superfrac tray, Maxfrac tray, dual flow tray, grid plate tray, turbogrid plate tray, Kittel tray, Oldershaw perforated plate, and the like, and such packings are preferably random packings, such as Raschig ring, Lessing ring, Pall ring, Berl saddle, Intalox saddle, Dixon packing, McMahon packing, and Heli Pack and regular packings, such as Mellapak, Gempak, TECHNO-PAK, FLEXI-PAK, Sulzer packing, Goodroll packing, and Glitchgrid. In the present invention, a reactive distillation column having both a tray part and a part filled with packings can also be used. The expression "the number of stages of internals: n" used in the present invention means the number of trays in the case of trays and the number of theoretical plates in the case of packings. Therefore, in the case of a reactive distillation column having both a tray part and a part filled with packings, n is a total of the number of trays and the number of theoretical plates.

In the present invention, as shown in FIG. 1, internals of the reaction distillation part of the reactive distillation column are trays, and particularly, the tray is more preferably a perforated plate tray having a perforated plate part and a downcomer part since it is superior in view of the function and the cost of equipment.

The perforated plate tray is preferably a perforated plate tray in which the number of holes per $m^2$ of the area of the perforated plate part is 150 to 1,200, more preferably a perforated plate tray in which the number of holes per $m^2$ of the area is 200 to 1,100, and particularly more preferably a perforated plate tray in which the number of holes per $m^2$ of the area is 250 to 1,000. The cross section per hole of the perforated plate tray is preferably 0.5 to 5 $cm^2$/hole, more preferably 0.7 to 4 $cm^2$/hole, and particularly preferably 0.9 to 3 $cm^2$/hole.

Materials constituting the reactive distillation column used in the present invention and trays to be used are mainly metal materials, such as carbon steel and stainless steel, and use of stainless steel is preferable in view of the stability of the quality of diethyl carbonate, which is the objective substance.

A reactive distillation column of the present invention is required to have a function to separate diethyl carbonate from a large amount of reaction mixtures at a specified separation efficiency continuously and stably for a long term. A reactive distillation column used for the method for producing diethyl carbonate of the present invention meets either of the design condition shown in the following [1] or [2], or the combination of them.

[1] The reaction mode is a countercurrent reaction mode in which a liquid or solid (including slurry) transesterification catalyst is made contact with a liquid or gaseous raw material for production in the column.

[2] Both raw material feed positions of dimethyl carbonate and ethanol, which are raw materials for producing, are located below (at the column bottom side) the catalyst feed position at which a transesterification catalyst is fed. As long as the raw material feed position is located below (at the column bottom side) the transesterification catalyst feed position, each of dimethyl carbonate and ethanol may be introduced from the same stage or another stage of the distillation column.

Advantageous effects of the present invention are solitary effects of the above described design condition or combined effects by an appropriate combination of both conditions. Under the reaction conditions that meet the above described [1] and/or [2], dimethyl carbonate, which is a raw material for production, can react at a satisfactory reaction yield without forming an azeotropic mixture with methanol, which was a conventional problem, and the efficiency of separation of a low-boiling compound from the objective substance can be ensured, leading to achievement of the objective specification and producing amount.

<Required Reaction Space in Reactive Distillation Column (Required Number of Reaction Stages: $\Delta N$; Required Reaction Distance: $\Delta L$)>

In the production method of the present invention, the space between the feed position of dimethyl carbonate and/or ethanol, which are raw materials for producing, (raw material introduction port: 16 in FIG. 1) and the transesterification catalyst feed position (catalyst introduction port: 14 in FIG. 1) is the required reaction space. This required reaction space can be calculated, for example, as the required number of reaction stages: $\Delta N$ in the case of a tray-type reactive distillation column in which internals of the reactive distillation column are separated by reaction stages (trays) or as the required reaction distance: $\Delta L$ in the case of a packing-type reactive distillation column in which internals are packings.

[1. Assumption of Reaction Model]

Figure 2:
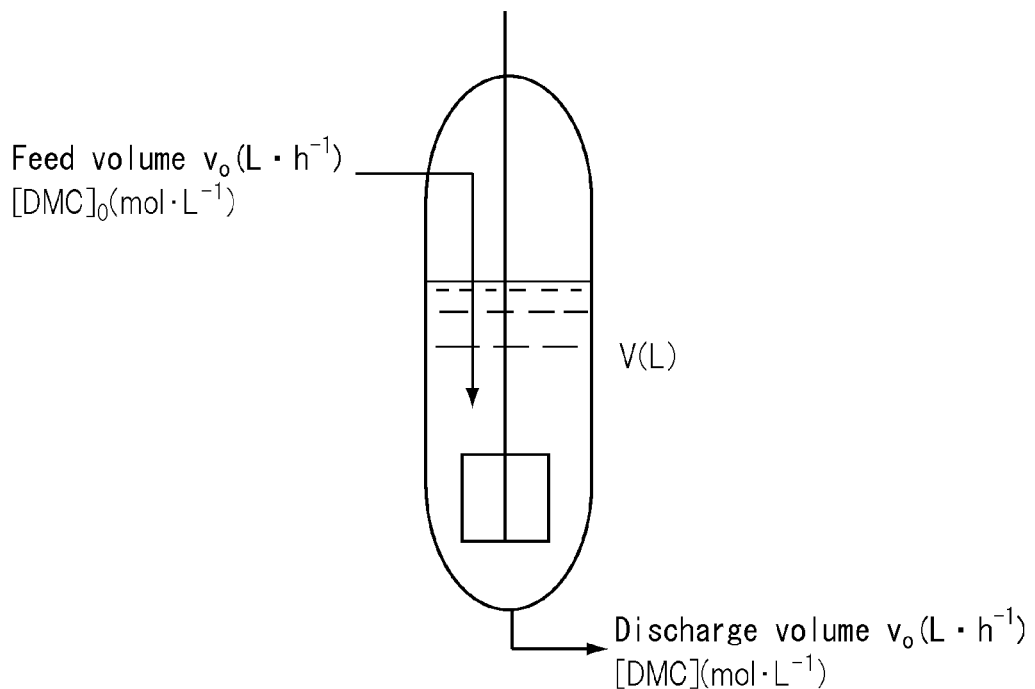
FIG. 2 is a schematic diagram showing a tray-type reactive distillation column of the present invention assumed as a continuous stirred-tank (single-tank) reactor.

The required reaction space in the producing apparatus of the present invention can be calculated by analyzing, as a reaction model, a "continuous tank-type reactor" as shown in FIG. 2 in which the space between the catalyst introduction port: 14 and the raw material introduction port: 16 of the reactive distillation column shown in FIG. 1 is considered as one reactor. In this case, the required reaction space is defined as a space in which dimethyl carbonate (DMC), which is a raw material, reacts at a specified DMC conversion rate (V in FIG. 2).

In the present invention, for a tray-type reactive distillation column, first, reaction conditions when the entire apparatus was assumed as a single-tank reactor were determined, and by using the conditions, the formula to calculate the required number of reaction stages: $\Delta N$ was identified.

[2. Calculation of DMC Conversion]

(2-1: Calculation of DMC Consumption Rate ($-r_{DMC}$))

Transesterification related to the present invention includes the first step chemical equilibrium transesterification represented by the following reaction scheme <I> in which dimethyl carbonate (DMC) is reacted with ethanol (EtOH) to be converted to ethyl methyl carbonate (EMC) in the presence of a transesterification catalyst, where methanol (MeOH) is produced as a by-product.

Reaction Scheme <I>:

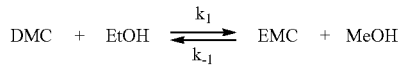

where $k_1$ represents the reaction rate constant of EMC synthesis reaction, and $k_{-1}$ represents the reaction rate constant of the reverse reaction of EMC synthesis reaction.

In the above transesterification, the DMC conversion rate: Conv is related to the DMC consumption rate: $-r_{DMC}$. The DMC consumption rate: $-r_{DMC}$ is represented by following equation (A):

$$-r_{DMC}=k_1[\text{Cat}][\text{DMC}][\text{EtOH}]-k_{-1}[\text{Cat}][\text{EMC}][\text{MeOH}] \qquad \text{Equation (A)}$$

where $-r_{DMC}$ represents the DMC consumption rate (mol·L$^{-1}$·h$^{-1}$), $k_1$ represents the reaction rate constant (L$^2$·mol$^{-2}$·h$^{-1}$) of EMC synthesis reaction, and $k_{-1}$ represents the reaction rate constant (L$^2$·mol$^{-2}$·h$^{-1}$) of the reverse reaction of EMC synthesis reaction. [Cat] represents the catalyst concentration (mol·L$^{-1}$) in the reactive distillation column, [DMC] represents the DMC concentration (mol·L$^{-1}$) in the reactive distillation column, [EtOH] represents the EtOH concentration (mol·L$^{-1}$) in the reactive distillation column, [EMC] represents the EMC concentration (mol·L$^{-1}$) in the reactive distillation column, and [MeOH] represents the MeOH concentration (mol·L$^{-1}$) in the reactive distillation column.

Since a large excess of EtOH is used for DMC in the production method of the present invention, EMC produced by the reaction scheme <I> can be considered to undergo the second step transesterification represented by the following reaction scheme <II> to be promptly converted to diethyl carbonate (DEC).

Reaction Scheme <II>:

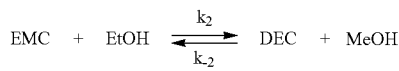

where $k_2$ represents the reaction rate constant of DEC synthesis reaction, and $k_{-2}$ represents the reaction rate constant of the reverse reaction of DEC synthesis reaction.

Namely, the reaction rate constant: $k_{-1}$ of the reverse reaction can be considered almost zero (0) in the reaction scheme <I>. If $k_{-1}$ is nearly equal to 0, the equation (A) is represented by equation (B).

$$-r_{DMC}=k_1[\text{Cat}][\text{DMC}][\text{EtOH}] \qquad \text{Equation (B)}$$

where $-r_{DMC}$, $k_1$, [Cat], [DMC], and [EtOH] are as defined above.

Since EtOH is partially distilled off by reflux from the column top part in the production method of the present invention, the net EtOH concentration remaining in the reactive distillation column cannot be decided by its feed volume. Therefore, the apparent reaction rate constant by considering the distilled volume of EtOH was set at $k_{01}$ defined as the product of the rate constant: $k_1$ and [EtOH] as shown in following equation (C). Then, this $k_{01}$ is substituted into the equation (B) to obtain equation (D).

$$k_{01}=k_1[\text{EtOH}] \qquad \text{Equation (C)}$$

where $k_{01}$ represents the apparent reaction rate constant (L·mol$^{-1}$·h$^{-1}$), and $k_1$ and [EtOH] are as defined above.

$$-r_{DMC}=k_{01}[\text{Cat}][\text{DMC}] \qquad \text{Equation (D)}$$

where $-r_{DMC}$, $k_{01}$, [Cat], and [DMC] are as defined above.

(2-2: Calculation of Retention Time ($\tau$) of DMC in Reaction Space)

If the reaction is supposed to be carried out in a steady state, in which the inflow into the reaction column is the same as the outflow from the reaction column, in a continuous tank-type reactor as shown in FIG. 2, the retention time: $\tau$ of the reaction solution in the reaction space is represented by the following equation (E) as a ratio of the volume of raw materials (DMC and EtOH, and a catalyst) fed into the reactive distillation column per unit time (raw material feed volume: $v_0$) to the volume of reaction solution retained in the reactive distillation column (volume of column solution: V) (Reference: Fundamental Chemical Engineering (*Kiso Kagaku Kogaku*), pp. 50, numerical expression (2.61); edited by the Society of Chemical Engineers; published by Baifukan Co., Ltd.; Jan. 22, 1999). Furthermore, the retention time $\tau$ in the reaction space can also be represented by the following equation (E) from the decreased volume of DMC and the DMC consumption rate: $-r_{DMC}$.

$$\tau = \frac{V}{v_0} = \frac{[DMC]_0 - [DMC]}{-r_{DMC}} \qquad \text{Equation (E)}$$

where $\tau$ represents the retention time (h) in the reaction space from FIG. 2, $v_0$ represents the raw material feed volume into the reactive distillation column per unit time (L·h$^{-1}$) from FIG. 2, and V represents the volume of column solution (L) in the reactive distillation column. $[DMC]_0$ represents the DMC concentration (mol·L$^{-1}$) in raw materials fed into the reactive distillation column, and [DMC] represents the concentration of outflowing DMC (mol·L$^{-1}$) outflowing from the column bottom of the reactive distillation column. $-r_{DMC}$ is as described above.

The raw material feed volume into the reactive distillation column: $v_0$ (L·h$^{-1}$) represents the total amount of the feed volume of raw materials (DMC and EtOH, and a catalyst) per unit time. For example, in the actual producing method using a tray-type reactive distillation column as shown in FIG. 1, DMC and EtOH, and a catalyst are separately fed, while in the reaction model in FIG. 2, the catalyst introduction port and the raw material introduction port are at the same reaction stage since the space between the catalyst introduction port: 14 and the raw material introduction port: 16 of the reactive distillation column shown in FIG. 1 is considered as one reactor. Therefore, $v_0$ is the total amount of the feed volume of raw materials (DMC and EtOH, and a catalyst).

V represents the volume of column solution (L) in the reactive distillation column. The volume of column solution: V in the reaction model in FIG. 2 corresponds to the fluid volume existing between the catalyst introduction port: 14 and the raw material introduction port: 16 of the reactive distillation column shown in FIG. 1.

Furthermore, $[DMC]_0$ represents the DMC concentration $(mol \cdot L^{-1})$ in raw materials fed into the reactive distillation column, and is a value set at the time of reaction. [DMC] represents the concentration of outflowing DMC $(mol \cdot L^{-1})$ outflowing from the column bottom of the reactive distillation column, and can be experimentally determined from the effluent.

When the equation (D) is substituted into the equation (E), the retention time: $\tau$ is represented by the equation (F).

$$\tau = \frac{[DMC]_0 - [DMC]}{k_{01}[Cat][DMC]} \qquad \text{Equation (F)}$$

where $\tau$, $[DMC]_0$, [DMC], $k_{01}$, and [Cat] are as defined above.

(2-3: Calculation of DMC Conversion Rate)

The raw material DMC conversion rate: Conv is represented by following equation (G) from the concentration of DMC fed into the reactive distillation column $[DMC]_0$ and the concentration of outflowing DMC outflowing from the column bottom of the reactive distillation column [DMC]. Conv is a real number of 0 to 1, and not a value represented by percentage (%).

$$Conv = \frac{[DMC]_0 - [DMC]}{[DMC]_0} = 1 - \frac{[DMC]}{[DMC]_0} \qquad \text{Equation (G)}$$

where Conv represents the reaction conversion rate of DMC, which is a raw material. $[DMC]_0$ and [DMC] are as defined above.

The equation (F) is transformed to make the equation (H), and equation (H) is substituted into the equation (G) to obtain equation (I).

$$\frac{[DMC]}{[DMC]_0} = \frac{1}{k_{01}\tau[Cat]+1} \qquad \text{Equation (H)}$$

where $[DMC]_0$, [DMC], $k_{01}$, [Cat], and $\tau$ are as defined above.

$$Conv = \frac{k_{01}\tau[Cat]}{k_{01}\tau[Cat]+1} \qquad \text{Equation (I)}$$

where Conv, $k_{01}$, [Cat], and $\tau$ are as defined above.

[3. Calculation of Reaction Rate Constant ($k_1$)]

The reaction rate constant: $k_1$ is expressed as following equation (J), by using a general Arrhenius equation.

$$k_1 = A\exp(-E/RT) \qquad \text{Equation (J)}$$

where A represents frequency factor $(L^2 \cdot mol^{-2} \cdot s^{-1})$, E represents energy of activation $(J \cdot mol^{-1})$, and R represents gas constant $(8.314\ J \cdot mol^{-1} \cdot K^{-1})$, and T represents temperature (K: Kelvin temperature).

The frequency factor: A and the energy of activation: E can be determined by appropriately sampling reaction solutions during reaction and by measuring the degree of progression of reaction calculated from the consumption of DMC. For example, in the present invention, A and E were determined as follows from the results obtained according to the method shown in Example 6.

$$A = 2.66 \times 10^5$$

$$E = 4.16 \times 10^4$$

A and E are unchanged constants in the reaction in which DEC is produced by reacting DMC with EtOH.

[4. Calculation of Apparent Reaction Rate Constant ($k_{01}$)]

Then, the apparent reaction rate constant: $k_{01}$ can be transformed to the following equation (K) represented by $k_{01}$ using the equation (J) and the equation (C).

$$k_{01} = A\exp(-E/RT)[EtOH] \qquad \text{Equation (K)}$$

where A, E, R, T, and [EtOH] are as defined above.

The apparent reaction rate constant: $k_{01}$ can be calculated by using values obtained by experiment (Conv, $\tau$, and [Cat]). More particularly, for example, by using the Conv, $\tau$, and [Cat] of the data shown in Table 1 of Examples, $k_{01}$ can be calculated from the equation (1). In this case, $k_{01}$ is preferably calculated so that the sum of square of the error between the actual value of the raw material DMC conversion rate: Conv and the calculated value of the DMC conversion rate is minimal by the least-squares method (see, for example, FIG. 3). In the calculation of $k_{01}$, the volume of reaction solution per reaction stage (tray) (hold-up volume: $V_h$) can be obtained from the designed value of the reaction stage (tray) if the scale of a reactor is large, while if a reactor is small or no design information on the reaction stage (tray) is available, it needs to be actually measured. A method for determining the volume of reaction solution per reaction stage (tray): $V_h$ by actual measurement includes, for example, a method in which reaction solutions retained on reaction stages (trays) after completion of reaction are recovered, their mass is measured, and the obtained value is divided by the number of reaction stages used to calculate $V_h$. By using this method, $V_h$ was calculated for the apparatus used in Example 1 described later also in the present invention. The volume of reaction solution in the reaction space in the reactive distillation column (hold-up volume: $V_H$) was calculated as $V_h \times$ the number of stages.

As a result, in the case of the reflux ratio: r of 0.5 to 10 excluding Comparative Example 3, the apparent reaction rate constant: $k_{01}$ according to the production method of the present invention was determined to be 6442 $L \cdot mol^{-1} \cdot h^{-1}$ (1.79 $L \cdot mol^{-1} \cdot s^{-1}$).

Furthermore, when the reaction temperature of transesterification is set at 78° C., which is the boiling point of EtOH under normal pressure, [EtOH] can be calculated from the equation (K) by using the $k_{01}$ previously calculated from the results of Examples. In this way, [EtOH]=10.38 $mol \cdot L^{-1}$ was obtained.

When A, E, R, and the obtained [EtOH] are substituted into the equation (K), the apparent reaction rate constant: $k_{01}$ can be represented by the equation (L) as a relation with reaction temperature T.

$$k_{01} = 3600 \times \exp(14.8311 - 5003.61/T) \qquad \text{Equation (L)}$$

where $k_{01}$ and T are as defined above.

Importantly, since the apparent reaction rate constant: $k_{01}$ can be represented by the equation (L) depending on temperature: T, this equation can be applied, for example, even when changes in column temperature occur due to the effects by operating pressure.

[5. Calculation of Required Number of Reaction Stages: ΔN]

The required number of reaction stages: ΔN (number of stages) is expressed like as following equation (M) from the volume of reaction solution in the reaction space in the reactive distillation column (hold-up volume: $V_H$) and the volume of reaction solution per reaction stage (hold-up volume: $V_h$).

$$\Delta N = \frac{V_H}{V_h} \qquad \text{Equation (M)}$$

where ΔN represents the required number of reaction stages (number of stages), and $V_h$ and $V_H$ are as defined above.

Since V in the reaction model in FIG. 2 is the same as the volume of reaction solution in the reaction space in the reactive distillation column (hold-up volume: $V_H$), ΔN can be expressed like as the following equation (N) using τ from the equation (E) and the equation (M) where V is $V_H$.

$$\Delta N = \frac{V}{V_h} = \frac{v_0}{V_h} \times \tau \qquad \text{Equation (N)}$$

where ΔN, τ, V, and $V_h$ are as defined above.

From the equation (I), τ is expressed like as following equation (O).

$$\tau = \frac{Conv}{k_{01}[Cat](1 - Conv)} \qquad \text{Equation (O)}$$

where τ, Conv, $k_{01}$, and [Cat] are as defined above.

From the equation (N) and the equation (O), ΔN is expressed like as the following equation (P).

$$\Delta N = \frac{v_0}{V_h} \times \frac{Conv}{k_{01}[Cat](1 - Conv)} \qquad \text{Equation (P)}$$

where ΔN, Conv, $v_0$, $V_h$, $k_{01}$, and [Cat] are as defined above.

Then, the catalyst concentration in the reactive distillation column: [Cat] is expressed like as the following equation (Q) using the catalyst feed amount into the reactive distillation column: c, the extraction volume from the column bottom of the reactive distillation column: B, the reflux ratio: r, and the extraction volume from the column top of the reactive distillation column: D.

$$[Cat] = \frac{c}{(B + rD)} \qquad \text{Equation (Q)}$$

where [Cat] is as described above. c represents the catalyst feed amount (mol·h$^{-1}$) into the reactive distillation column, B represents the extraction volume (L·h$^{-1}$) from the column bottom of the reactive distillation column, r represents the reflux ratio (dimensionless), and D represents the extraction volume (L·h$^{-1}$) from the column top of the reactive distillation column.

[6. Calculation of Required Reaction Space (Required Number of Reaction Stages: ΔN; Required Reaction Distance: ΔL)]

<Required Number of Reaction Stages: ΔN>

From the equation (P) and the equation (Q), the required reaction space of the producing apparatus that carry out the reaction of the present invention can be represented by the following inequality expression (R) as the required number of reaction stages: ΔN. Furthermore, it can be represented by the inequality expression (R') using the $k_{01}$ of the equation (K).

$$\Delta N \geq \frac{v_0}{V_h} \times \frac{Conv}{k_{01} \times \frac{c}{B + rD} \times (1 - Conv)} \qquad \text{Inequality Expression (R)}$$

where ΔN, $v_0$, $V_h$, Conv, $k_{01}$, c, B, r, and D are as defined above.

$$\Delta N \geq \frac{v_0}{V_h} \times \frac{Conv}{A\exp(-E/RT)[EtOH] \times \frac{c}{B + rD} \times (1 - Conv)} \qquad \text{Inequality Expression (R')}$$

where ΔN, $v_0$, $V_h$, Conv, A, E, R, T, [EtOH], c, B, r, and D are as defined above.

Here, when the apparent reaction rate constant: $k_{01}$ of the equation (L) is substituted into the inequality expression (R), the required number of reaction stages: ΔN when the production method of the present invention is carried out using a tray-type reactive distillation apparatus is expressed like as the following inequality expression (S).

$$\Delta N \geq \frac{v_0}{V_h} \times \frac{Conv}{3600 \times \exp(14.8311 - 5003.61/T) \times \frac{c}{B + rD} \times (1 - Conv)} \qquad \text{Inequality Expression (S)}$$

where ΔN, $v_0$, $V_h$, T, c, B, r, D, and Conv are as defined above.

When the boiling point (78° C.=351 K) of EtOH is substituted into the inequality expression (S) by assuming that transesterification is usually carried out under normal pressure and the reflux conditions of EtOH, the following inequality expression (S') is obtained.

$$\Delta N \geq \frac{v_0}{V_h} \times \frac{Conv}{6404.71 \times \frac{c}{B + rD} \times (1 - Conv)} \qquad \text{Inequality Expression (S')}$$

where ΔN, $v_0$, $V_h$, c, B, r, D, and Conv are as defined above.

By identifying B (the extraction volume from the column bottom of the reactive distillation column), D (the extraction volume from the column top of the reactive distillation column), and $V_h$ (the hold-up volume per reaction stage) from the design (specification) of the reactive distillation column actually used, and by setting $v_0$ (the feed volume of DMC, EtOH, and a transesterification catalyst), c (the catalyst feed amount into the reactive distillation column), T (column temperature), and r (reflux ratio) from the reaction conditions to substitute the objective DMC reaction conversion rate: Conv into the inequality expression (S), the required number of reaction stages: ΔN when the production method of the present invention is carried out using a tray-type reactive distillation apparatus can be calculated.

From the above, the present invention also includes a method for calculating the required number of reaction stages: ΔN when DEC is produced using a tray-type reactive distillation apparatus by setting the designed value of the reactive distillation column, reaction conditions, and the objective DMC reaction conversion rate.

In addition, the present invention also includes a method for calculating the DMC reaction conversion rate when DEC is produced using a tray-type reactive distillation apparatus by setting the designed value of the reactive distillation column, reaction conditions, and the required number of reaction stages: ΔN.

As an example, when the DMC reaction conversion rate is 88.5% or more (Conv≥0.885), the inequality expression (S) is expressed like as the following inequality expression ($S^{88.5\%}$).

$$\Delta N \geq 2.138 \times 10^{-3} \times \frac{v_0}{V_h} \times \frac{(B + rD)}{c \times \exp(14.8311 - 5003.61/T)} \qquad \text{Inequality Expression } (S^{88.5\%})$$

where ΔN, $v_0$, $V_h$, T, c, B, r, and D are as defined above.

Furthermore, when the column temperature T is the boiling point (78° C.=351 K) of EtOH, the inequality expression (S) is expressed like as the following inequality expression ($S^{88.5\%, 78°\,C.}$).

$$\Delta N \geq 1.202 \times 10^{-3} \times \frac{v_0}{V_h} \times \frac{(B + rD)}{c} \qquad \text{Inequality Expression } (S^{88.5\%, 78°C.})$$

where ΔN, $v_0$, $V_h$, c, B, r, and D are as defined above.

Therefore, from the inequality expression ($S^{88.5\%, 78°\,C.}$), if the scale of the reactor and the feed volume of raw materials to be used and reflux ratio are set, the required number of reaction stages: ΔN in which DEC can be produced at a DMC reaction conversion rate of 88.5% or more can be set from the inequality expression ($S^{88.5\%, 78°\,C.}$).

<Required Reaction Distance: ΔL>

When a packing-type reactive distillation column is used as a reactive distillation column, the distance between the catalyst introduction port and the raw material introduction port of the reactive distillation column: ΔL is represented by the following equation (T) using the hold-up volume: d per meter in the region between the catalyst introduction port and the raw material introduction port of the reactive distillation column.

$$\Delta L = \frac{V_H}{d} \qquad \text{Equation (T)}$$

where ΔL represents the distance (m) between the catalyst introduction port and the raw material introduction port of the reactive distillation column, and d represents the hold-up volume ($L \cdot m^{-1}$) per meter in the region between the catalyst introduction port and the raw material introduction port of the reactive distillation column. $V_H$ is as described above.

The retention time: τ in the reaction space of DMC fed into the reactive distillation column is represented by the equation (E). Here, since V in the reaction model in FIG. 2 is the same as the volume of reaction solution in the reaction space in the reactive distillation column (hold-up volume: $V_H$), ΔL can be expressed like as the equation (U) using τ from the equation (E), the equation (O), and the equation (T) where V is $V_H$.

$$\Delta L = \frac{v_0}{d} \times \tau = \frac{v_0}{d} \times \frac{Conv}{k_{01}[Cat](1 - Conv)} \qquad \text{Equation (U)}$$

where ΔL, Conv, τ, $v_0$, d, $k_{01}$, and [Cat] are as defined above.

When the equation (Q) is substituted into the equation (U) and the $k_{01}$ of the equation (K) is used, the required reaction distance: ΔL can be represented by following inequality expression (V).

$$\Delta L \geq \frac{v_0}{d} \times \frac{Conv}{A\exp(-E/RT)[EtOH] \times \frac{c}{B+rD} \times (1 - Conv)} \qquad \text{Inequality Expression (V)}$$

where ΔL, $v_0$, d, A, E, R, T, c, B, r, D, Conv, and [EtOH] are as defined above.

When the apparent reaction rate constant: $k_{01}$ of the equation (L) is substituted into the inequality expression (V), the required reaction distance: ΔL is expressed like as inequality expression (W).

$$\Delta L \geq \frac{v_0}{d} \times \frac{Conv}{3600 \times \exp(14.8311 - 5003.61/T) \times \frac{c}{B+rD} \times (1 - Conv)} \qquad \text{Inequality Expression (W)}$$

where ΔL, $v_0$, d, T, c, B, r, D, and Conv are as defined above.

When the boiling point (78° C.=351 K) of EtOH is substituted into the inequality expression (W) by assuming that transesterification is usually carried out under normal pressure and the reflux conditions of EtOH, the following inequality expression (W') is obtained.

$$\Delta L \geq \frac{v_0}{d} \times \frac{Conv}{6404.71 \times \frac{c}{B+rD} \times (1 - Conv)} \qquad \text{Inequality Expression (W')}$$

where ΔL, $v_0$, d, c, B, r, D, and Conv are as defined above.

By identifying B (the extraction volume from the column bottom of the reactive distillation column), D (the extraction volume from the column top of the reactive distillation column), and d (the hold-up volume per meter in the region between the catalyst introduction port and the raw material introduction port of the reactive distillation column) from the design (specification) of the reactive distillation column actually used, and by setting $v_0$ (the feed volume of DMC, EtOH, and a transesterification catalyst), c (the catalyst feed amount into the reactive distillation column), T (column temperature), and r (reflux ratio) from the reaction conditions to substitute the objective DMC reaction conversion rate: Conv into the inequality expression (W), the required reaction distance: ΔL when the production method of the present invention is carried out using a packing-type reactive distillation apparatus can be calculated.

From the above, the present invention also includes a method for calculating the required reaction distance: ΔL when DEC is produced using a packing-type reactive distillation apparatus by setting the designed value of the reactive distillation column, reaction conditions, and the objective DMC reaction conversion rate.

In addition, the present invention also includes a method for calculating the DMC reaction conversion rate when DEC is produced using, for example, a reactive distillation apparatus, such as a packing-type reactive distillation apparatus, other than a tray-type reactive distillation apparatus by setting the designed value of the reactive distillation column, reaction conditions, and the required reaction distance: ΔL.

As an example, when the DMC reaction conversion rate is 88.5% or more (Conv≥0.885), the inequality expression (W) is expressed like as the following inequality expression ($W^{88.5\%}$).

Inequality Expression ($W^{88.5\%}$)

$$\Delta L \geq 2.138 \times 10^{-3} \times \frac{v_0}{d} \times \frac{(B+rD)}{c \times \exp(14.8311 - 5003.61/T)}$$

where ΔL, $v_0$, d, T, c, B, r, and D are as defined above.

Furthermore, when the column temperature: T is the boiling point (78° C.=351 K) of EtOH, the inequality expression (W) is expressed like as the following inequality expression ($W^{88.5\%,78°C.}$).

Inequality Expression ($W^{88.5\%,78°C.}$):

$$\Delta L \geq 1.202 \times 10^{-3} \times \frac{v_0}{d} \times \frac{(B+rD)}{c}$$

where ΔL, $v_0$, d, c, B, r, and D are as defined above.

Therefore, from the inequality expression ($W^{88.5\%,78°C.}$) if the scale of the reactor and the feed volume of raw materials to be used and reflux ratio are set, the required reaction distance: ΔL in which DEC can be produced at a DMC reaction conversion rate of 88.5% or more can be set from the inequality expression ($W^{88.5\%,78°C.}$).

A reactive distillation column of the present invention is required to have a function to separate diethyl carbonate from a large amount of reaction mixtures at a specified separation efficiency continuously and stably for a long term. A reactive distillation column used for the method for producing diethyl carbonate of the present invention meets any of the design conditions shown in the following [3] to [10], or the combination of them.

[3] A tray-type reactive distillation column is used, the reflux ratio: r is 0.5 to 10, and the required number of reaction stages: ΔN meets the following inequality expression (S).

Inequality Expression (S):

$$\Delta N \geq \frac{v_0}{V_h} \times \frac{Conv}{3600 \times \exp(14.8311 - 5003.61/T) \times \frac{c}{B+rD} \times (1-Conv)}$$

where ΔN, $v_0$, $V_h$, T, c, B, r, D, and Conv are as defined above.

[4] A tray-type reactive distillation column is used, the reflux ratio: r is 0.5 to 10, the column temperature: T is the boiling point of EtOH under normal pressure, and the required number of reaction stages: ΔN meets the following inequality expression (S').

Inequality Expression (S'):

$$\Delta N \geq \frac{v_0}{V_h} \times \frac{Conv}{6404.71 \times \frac{c}{B+rD} \times (1-Conv)}$$

where ΔN, $v_0$, $V_h$, c, B, r, D, and Conv are as defined above.

[5] When a tray-type reactive distillation column is used, the required number of reaction stages: ΔN is determined from the inequality expression (R').

Inequality Expression (R'):

$$\Delta N \geq \frac{v_0}{V_h} \times \frac{Conv}{A \, \exp(-E/RT)[\text{EtOH}] \times \frac{c}{B+rD} \times (1-Conv)}$$

where ΔN, $v_0$, $V_h$, Conv, A, E, R, T, [EtOH], c, B, r, and D are as defined above.

[6] The number of stages of a tray-type reactive distillation column: n is, in terms of the number of actual stages, usually 1 to 100, preferably 10 to 75, more preferably 30 to 75, still more preferably 33 to 50, and particularly preferably 33 to 40.

The number of stages of a packing-type reactive distillation column: n is, in terms of the number of theoretical plates, usually 1 to 100, preferably 32 to 75, more preferably 33 to 60, still more preferably 33 to 50, and particularly preferably 33 to 40.

In the production method of the present invention, reaction can be carried out similarly even when the number of stages: n (in terms of the number of actual stages or in terms of the number of theoretical plates) is 100 or more, but increase in the number of stages are associated with increase in the length of the reaction distillation part of the reactive distillation column to be used, resulting in too large differences in pressure between the upper and lower of the column and necessity of increasing temperature in the lower column part, which is not economical. Therefore, if the number of stages is increased, it is designed by considering the height limitation, equipment cost, utility cost, and the like when a reactor is produced.

[7] For example, if the number of all trays is 1 to 100, the space between the raw material introduction port and the catalyst introduction port: ΔN is usually 1 to 50, preferably 5 to 35, more preferably 10 to 35, still more preferably 10 to 30, and particularly preferably 15 to 30.

Under the above described conditions, dimethyl carbonate can be react at a satisfactory reaction yield without forming an azeotropic mixture with methanol, and the efficiency of separation of a low-boiling compound from the objective substance can be ensured, leading to achievement of the objective specification and producing amount. In the production method of the present invention, reaction can be carried out with the similar efficacy even when the space between the raw material introduction port and the catalyst introduction port is 50 or more in terms of the number of actual stages or in terms of the number of theoretical plates, but increase in the number of stages are associated with increase in the column length of the reactive distillation column to be used, resulting in too large differences in pressure between the upper and lower of the column; thus a long-term stable operation is difficult and the temperature in the lower column part should be raised, which is not economical. For example, when the number of all trays of the producing apparatus of the present invention is not more than 100, the raw material introduction port is particularly preferably located below (at the column bottom side) the 15th stage (for example, between 14th and 15th stages) from the column top part.

[8] A packing-type reactive distillation column is used, the reflux ratio: r is 0.5 to 10, and the required reaction distance: $\Delta L$ meets inequality expression (W).

Inequality Expression (W):

$$\Delta L \geq \frac{v_0}{d} \times \frac{Conv}{3600 \times \exp(14.8311 - 5003.61/T) \times \frac{c}{B+rD} \times (1 - Conv)}$$

where $\Delta L$, $v_0$, d, T, c, B, r, D, and Conv are as defined above.

[9] A packing-type reactive distillation column is used, the reflux ratio: r is 0.5 to 10, the column temperature: T is the boiling point of EtOH under normal pressure, and the required reaction distance: $\Delta L$ meets the following inequality expression (W').

Inequality Expression (W'):

$$\Delta L \geq \frac{v_0}{d} \times \frac{Conv}{6404.71 \times \frac{c}{B+rD} \times (1 - Conv)}$$

where $\Delta L$, $v_0$, d, c, B, r, D, and Conv are as defined above.

[10] When a packing-type reactive distillation column is used, the required reaction distance: $\Delta L$ is determined from the inequality expression (V).

Inequality Expression (V):

$$\Delta L \geq \frac{v_0}{d} \times \frac{Conv}{A \exp(-E/RT)[EtOH] \times \frac{c}{B+rD} \times (1 - Conv)}$$

where $\Delta L$, $v_0$, d, A, E, R, T, c, B, r, D, Conv, and [EtOH] are as defined above.

[11] The ratio of the spatial volume (m$^3$) between the raw material feed position and the catalyst feed position (RH in FIG. 1) to the spatial column volume (the spatial volume (m$^3$) in the reaction distillation part; RD in FIG. 1) is usually 0.01 to 1.00, preferably 0.1 to 0.9, more preferably 0.2 to 0.8, still more preferably 0.25 to 0.75, and particularly preferably 0.5 to 0.75.

One embodiment of the present invention relates to a method for continuously producing diethyl carbonate by transesterification of dimethyl carbonate with ethanol in a reactive distillation column.

<Dimethyl Carbonate>

Regarding dimethyl carbonate used as a raw material for production in the present invention, although a commercially available product can be used, various types of dimethyl carbonate produced by publicly known methods, such as, for example, that obtained by vapor-phase contact reaction between carbon monoxide and a nitrite ester in the presence of a solid catalyst with reference to Kokai (Japanese Unexamined Patent Publication) No. 3-141243 and that obtained by reaction between carbon dioxide and alcohol in the presence of a solid catalyst with reference to Kokai (Japanese Unexamined Patent Publication) No. 2006-176412.

<Ethanol>

Regarding ethanol used as a raw material for production in the present invention, although a commercially available product can be used, ethanol with a water content of 0.20% by weight or less (2,000 ppm or less) is preferably used so that transesterification in the present invention is not affected. Water contained is removed by, for example, dehydration operation and the like with desiccants, such as molecular sieve, anhydrous magnesium sulfate, and/or calcium oxide.

The amount of ethanol used for 1 mol of dimethyl carbonate is preferably 1.8 to 10 mol, more preferably 2.0 to 8.0 mol, still more preferably 2.0 to 6.0 mol, and particularly preferably 2.0 to 5.0 mol. Too small an amount of ethanol leads to inefficient progression of reaction, while too large an amount leads to more complications in removal after the reaction and is not preferable in view of economy (cost). Within the above described range of use amount, the reaction of the present invention can be carried out satisfactorily, and the use amount is suitable in view of economy.

<Transesterification Catalyst>

A transesterification catalyst used in the present invention includes preferably at least one of transesterification catalysts selected from the group consisting of an alkali metal hydroxide, an alkali metal carbonate compound, an alkali metal methoxide, and an alkali metal ethoxide, more preferably at least one of transesterification catalysts selected from the group consisting of lithium hydroxide, potassium hydroxide, sodium hydroxide, potassium carbonate, sodium carbonate, an alkali metal methoxide, and an alkali metal ethoxide, still more preferably at least one of transesterification catalysts selected from the group consisting of an alkali metal methoxide and an alkali metal ethoxide, and particularly preferably at least one of transesterification catalysts selected from the group consisting of lithium methoxide, sodium methoxide, potassium methoxide, lithium ethoxide, sodium ethoxide, and potassium ethoxide. These transesterification catalysts may be used alone or in a mixture with two or more of them, and furthermore, a commercially available product may be used, or they may be used by conventional purification separately.

These transesterification catalysts, for example, can be used as homogeneous catalysts when dissolved in ethanol, which is a raw material for production, or methanol, which is a reaction by-product, and as slurry catalysts when partially dissolved or dispersed in ethanol or methanol.

The amount of a transesterification catalyst used for 1 mol of dimethyl carbonate is usually 0.5 to 1,000 mmol, preferably 1 to 250 mmol, more preferably 2 to 50 mmol, still more preferably 2 to 25 mmol, and particularly preferably 2 to 15 mmol. Too small amount of a transesterification catalyst leads to no efficient progression of reaction, while too large amount leads to more complications in removing after the reaction and is not preferable in view of economy (cost). Within the above described range of use amount, the reaction of the present invention can be carried out satisfactorily, and the use amount is suitable in view of economy.

The reactive distillation using a reactive distillation column used in the present invention is required to have a function to separate diethyl carbonate from a large amount of reaction mixtures at a specified separation efficiency continuously and stably for a long term. In the method for producing diethyl carbonate of the present invention, reaction conditions in the reactive distillation column meet any of the various conditions shown in the following [12] to [16], or the combination of them.

[12] (Method for Feeding Dimethyl Carbonate and Ethanol)

In the present invention, there is no particular limitation on a method for feeding dimethyl carbonate and ethanol into the reactive distillation column, and dimethyl carbonate and ethanol can be fed as a liquid, gas, or a gas-liquid mixture.

In the present invention, dimethyl carbonate and ethanol can be intermittently or continuously fed into the reactive distillation column at a position below the feed position of a transesterification catalyst. Raw materials for production containing dimethyl carbonate and ethanol may contain methanol and/or methyl ethyl carbonate.

[13] (Method for Feeding Transesterification Catalyst)

In the present invention, there is no particular limitation on a method for feeding a transesterification catalyst into the reactive distillation column, for example, a transesterification catalyst may be fed as a liquid or as a solution or slurry in which it is dissolved or suspended in ethanol or methanol. Furthermore, a transesterification catalyst may contain, for example, methanol and/or ethanol, dimethyl carbonate, methyl ethyl carbonate, diethyl carbonate, and the like.

In the present invention, a transesterification catalyst can be intermittently or continuously fed into the reactive distillation column at a position above the feed position of a raw material for production.

[14] (Column Temperature)

In the reactive distillation of the present invention, although there is no particular limitation on the column temperature since it varies depending on pressure, for example, the temperature in the column top part: X and the reaction distillation part: RD is preferably 60° C. to 100° C. (i.e., the boiling point of ethanol (78° C.)±20° C.), more preferably 65° C. to 95° C. (the boiling point of ethanol (78° C.)±about 15° C.), and particularly preferably 70° C. to 90° C. (the boiling point of ethanol (78° C.)±about 10° C.). The temperature in the concentrating part: RC is preferably 105° C. to 150° C. (the boiling point of diethyl carbonate (° C.)±about 20° C.), more preferably 110° C. to 145° C. (the boiling point of diethyl carbonate (° C.)±15° C.), and particularly preferably 115° C. to 140° C. (the boiling point of diethyl carbonate (° C.)±about 10° C.). Since the temperature conditions varies depending on the shape or the number of stages of internals of a reactive distillation column, the type, composition, and quantity of a low-boiling reaction mixture fed, the purity of diethyl carbonate to be separated, and the like, the temperature conditions can be appropriately adjusted within the above described temperature range.

[15] (Column Pressure)

In the reactive distillation of the present invention, although the column pressure varies depending on the column top pressure, column composition, and/or column temperature, the pressure in the column top part: X and the concentrating part: RC is preferably normal pressure to 1,000 kPa (absolute pressure).

[16] (Reflux Ratio)

In the reactive distillation of the present invention, the reflux ratio: r of the reactive distillation column is preferably within a range of 0.5 to 10, more preferably 0.8 to 5, and still more preferably 1.5 to 4.0.

In the present invention, as described above, by feeding dimethyl carbonate and ethanol, which are raw materials for production, into a reactive distillation column related to the present invention, diethyl carbonate can be produced at a high reaction yield in the reaction space in which the conversion rate of dimethyl carbonate is preferably 90% or more, and more preferably 95% or more, with little loss of dimethyl carbonate, which is a raw material for production, from the column top part as an azeotropic mixture with methanol produced by the reaction.

<Diethyl Carbonate Produced by the Present Invention>

Diethyl carbonate produced by using a reactive distillation column of the present invention is obtained in the concentrating part: RC in FIG. 1 as a reaction concentrate together with a transesterification catalyst and the like. By separating and removing a transesterification catalyst contained in the obtained reaction concentrate, for example, by simple operations, such as washing with water, distillation with a thin-film distillation apparatus, and the like, high-purity diethyl carbonate can be obtained. Diethyl carbonate obtained by such way is, for example, a transparent liquid with a hue (APHA value) of 10 or less, and can usually be obtained as an ultra-high purity product of 97% by weight or more, preferably 99% by weight or more, and more preferably 99.9% by weight or more.

The content of reaction by-products of, for example, ether compounds, aldehyde compounds, and the like is 1% by weight or less of diethyl carbonate, preferably 0.5% by weight or less, more preferably 0.1% by weight or less, and still more preferably 0.05% by weight or less. Furthermore, the content of metal impurities (Na, K, Ca, Fe, Al, Mg, Cu, Pb) is usually 0.5 ppm or less, preferably 0.1 ppm or less, and more preferably 1 ppb or less.

In this way, according to the production method of the present invention, usually, diethyl carbonate of an ultra-high purity product of 97% by weight or more, preferably 99% by weight or more, and more preferably 99.9% by weight or more can be easily obtained.

Diethyl carbonate of the present invention obtained in this way can be used, for example, not only as raw materials for producing dyes, pigments, pharmaceuticals/agricultural chemicals, and organic materials in the electrical and electronic field (e.g., polycarbonate and the like) and solvents for synthesis of them, but also as cleaners for printing, additives of soil modifying agents, components of battery electrolytes, and the like.

EXAMPLES

The present invention will be described in detail below by way of Examples, but the present invention is not limited to these Examples.

In these Examples, all qualitative and quantitative analyses (internal standard substance is ethylbenzene) of the consumption of dimethyl carbonate, which is a raw material for production, the production of diethyl carbonate, which is the objective substance, and the like were carried out by using gas chromatography (GC) (GC-2014, manufactured by Shimadzu Corporation; GC column, TC-WAX 30 m×0.53 mm; GC detector, FID). The reaction conversion rate of dimethyl carbonate, which is a raw material for production, and the reaction selectivity and reaction yield of diethyl carbonate, which is the objective substance, were calculated by using the following equations (III) to (V), respectively.

Equation (III):

Reaction conversion rate of dimethyl carbonate (%) =

$$\frac{[\text{Consumption amount of dimethyl carbonate (mol)}]^{*1}}{[\text{Use amount of dimethyl carbonate (mol)}]} \times 100\ (\%)$$

*1: From quantitative analysis (GC), the above consumption amount or use amount was calculated as the number of moles.

Equation (IV):

Reaction selectivity of diethyl carbonate (%) =

$$\frac{[\text{Production of diethyl carbonate (mol)}]^{*1}}{[\text{Consumption of dimethyl carbonate (mol)}]} \times 100\ (\%)$$

*1: From quantitative analysis (GC), the above described production amount or use amount was calculated as the number of moles.

Equation (V):

Reaction yield of diethyl carbonate (%) =

$$\frac{[\text{Reaction conversion rate of dimethyl carbonate (\%)}] \times [\text{Reaction selectivity of diethyl carbonate (\%)}]}{100}\ (\%)$$

Example 1

Production of Diethyl Carbonate: ΔN=30

[Production Apparatus]

A producing apparatus used in the Example is a reactive distillation column shown in FIG. 1 with the following dimension.

A reactive distillation column with a column diameter (D1 in FIG. 1) of 34 mm, a tray space (L3 in FIG. 1) of 30 mm, the number of actual stages (n in FIG. 1) of 40 was used.

As an internal in the column, an Oldershaw perforated plate (tray diameter of 32 mm, hole diameter of 0.8 mm, opening ratio of 5.2%, manufactured by Asahi Seisakusho Co., Ltd.) was used.

[Reaction Method]

A raw material for production composed of dimethyl carbonate (DMC) and ethanol (EtOH) (mass ratio: EtOH (% by weight)/DMC (% by weight)=49.86/50.14) was continuously fed at a feed rate of 87.3 g/hr from the raw material introduction port (M in FIG. 1) between the 32th and 33th trays from the column top of the reactive distillation column.

Simultaneously, a sodium methoxide (MeONa) solution (mass ratio: MeONa (% by weight)/MeOH (% by weight)/EtOH (% by weight)=1.32/3.40/95.28) as a transesterification catalyst was continuously fed at a feed rate of 27.1 g/hr from the catalyst introduction port (C in FIG. 1) between the 2nd and 3rd trays from the column top of the reactive distillation column.

At the above described feed rates, under reaction conditions of the reactive distillation column including under normal pressure, column top temperature of 69° C. to 71° C., column temperature of 71° C. to 78° C. (measurement site: 25th tray from the column top), column bottom temperature of 105° C. to 120° C., and reflux ratio of 2.7, reactive distillation was continuously carried out.

After the above described reaction was carried out continuously for 6 hours, a solution that was continuously distilled out at a rate of 58.0 g/hr from the column top distillation port (T in FIG. 1) of the reactive distillation column was recovered and an analysis of the contents showed that methanol was 52.3% by weight, ethanol was 42.6% by weight, dimethyl carbonate was 1.9% by weight (2.5% by weight for the raw material feed amount), ethyl methyl carbonate was 2.7% by weight, and the others were 0.5% by weight (the reaction conversion rate of dimethyl carbonate: 97%). A solution that was continuously extracted out at a rate of 56.4 g/hr from the column bottom part (B in FIG. 1) of the reactive distillation column was recovered and an analysis of the contents showed that ethanol was 4.0% by weight, ethyl methyl carbonate was 1.8% by weight, diethyl carbonate was 93.7% by weight, and the others were 0.5% by weight (the reaction yield of diethyl carbonate: 92%).

Example 2

Production of Diethyl Carbonate: ΔN=20

[Production Apparatus]

The reactive distillation column same as in Example 1 was used.

<Reaction Method>

A raw material for production composed of dimethyl carbonate (DMC) and ethanol (EtOH) (mass ratio: EtOH (% by weight)/DMC (% by weight)=49.47/50.53) was continuously fed at a rate of 90.0 g/hr from the raw material introduction port (M in FIG. 1) between the 32th and 33th trays from the column top of the reactive distillation column.

Simultaneously, a sodium methoxide (MeONa) solution (mass ratio: MeONa (% by weight)/MeOH (% by weight)/EtOH (% by weight)=0.72/1.86/97.42) as a transesterification catalyst was also continuously fed at a rate of 27.6 g/hr from the catalyst introduction port (C in FIG. 1) between the 12th and 13th trays from the column top of the reactive distillation column.

At the above described feed rates, under reaction conditions of the reactive distillation column including under normal pressure, column top temperature of 69° C. to 72° C., column temperature of 72° C. to 78° C. (25th tray), column bottom temperature of 105° C. to 120° C., and reflux ratio: r of 2.1, reactive distillation was continuously carried out.

After the above described reaction was carried out continuously for 6 hours, a solution that was continuously distilled out at a rate of 63.5 g/hr from the column top distillation port (T in FIG. 1) of the reactive distillation column was recovered and an analysis of the contents showed that methanol was 46.1% by weight, ethanol was 45.2% by weight, dimethyl carbonate was 4.5% by weight (6.3% by weight for the raw material feed amount), ethyl methyl carbonate was 4.0% by weight, and the others were 0.2% by weight (the reaction conversion rate of dimethyl carbonate: 94%). A solution that was continuously extracted out at a rate of 54.1 g/hr from the column bottom part (B in FIG. 1) of the reactive distillation column was recovered and an analysis of the contents showed that ethanol was 2.3% by weight, ethyl methyl carbonate was 3.5% by weight, diethyl carbonate was 93.7% by weight, and the others were 0.5% by weight (the reaction yield of diethyl carbonate: 86%).

Example 3

Production of Diethyl Carbonate: ΔL=0.55 m

[Production Apparatus]

In Example 3, a packing-type reactive distillation column with the following dimension was used.

A reactive distillation column with a column diameter of 30 mm, a packing height of the concentrating part of 550 mm, and a packing height of the recovering part of 330 mm (in this Example, a total of the packing height of the concentrating part and the packing height of the recovering part corresponds to L1 in FIG. 1) was used.

As an internal, Sluzer laboratory packing EX (Sluzer Chemtech Ltd.), which is a regular packing, was used.

[Reaction Method]

A raw material for production composed of dimethyl carbonate (DMC) and ethanol (EtOH) (mass ratio: EtOH (% by weight)/DMC (% by weight)=49.95/50.05) was continuously fed at a rate of 82.6 g/hr from a raw material introduction port between the concentrating part and the recovering part of the reactive distillation column.

Simultaneously, a sodium methoxide (MeONa) solution (mass ratio: MeONa (% by weight)/MeOH (% by weight)/EtOH (% by weight)=0.68/1.76/97.56) as a transesterification catalyst was also continuously fed at a rate of 25.2 g/hr from a catalyst introduction port at the column top of the reactive distillation column.

At the above described feed rates, under reaction conditions of the reactive distillation column including under normal pressure, column top temperature of 69° C. to 75° C., column temperature of 75° C. to 78° C. (the raw material for production introduction part), column bottom temperature of 100° C. to 120° C., and reflux ratio: r of 3.2, reactive distillation was continuously carried out.

After the above described reaction was carried out continuously for 6 hours, a solution that was continuously distilled out at a rate of 59.4 g/hr from the column top distillation port of the reactive distillation column was recovered and an analysis of the contents showed that methanol was 43.6% by weight, ethanol was 44.0% by weight, dimethyl carbonate was 5.8% by weight (8.3% by weight for the raw material feed amount), ethyl methyl carbonate was 6.0% by weight, and the others were 0.6% by weight (the reaction conversion rate of dimethyl carbonate: 92%). A solution that was continuously extracted out at a rate of 48.1 g/hr from the column bottom part of the reactive distillation column was recovered and an analysis of the contents showed that ethanol was 6.2% by weight, ethyl methyl carbonate was 2.0% by weight, diethyl carbonate was 91.6% by weight, and the others were 0.2% by weight (the reaction yield of diethyl carbonate: 83%).

Example 4

Production of Diethyl Carbonate: ΔN=10

[Production Apparatus]

The reactive distillation column the same as in Example 1 was used.

[Reaction Method]

A raw material for production composed of dimethyl carbonate (DMC) and ethanol (EtOH) (mass ratio: EtOH (% by weight)/DMC (% by weight)=49.47/50.53) was continuously fed at a rate of 89.3 g/hr from the raw material introduction port (M in FIG. 1) between the 32th and 33th trays from the column top of the reactive distillation column.

Simultaneously, a sodium methoxide (MeONa) solution (mass ratio: MeONa (% by weight)/MeOH (% by weight)/EtOH (% by weight)=0.72/1.86/97.42) as a transesterification catalyst was also continuously fed at a rate of 27.5 g/hr from the catalyst introduction port (C in FIG. 1) between the 22th and 23th trays from the column top of the reactive distillation column.

At the above described feed rates, under reaction conditions of the reactive distillation column including under normal pressure, column top temperature of 69° C. to 72° C., column temperature of 72° C. to 78° C. (the space between the 24th and 25th trays), column bottom temperature of 105° C. to 120° C., and reflux ratio: r of 2.4, reactive distillation was continuously carried out.

After the above described reaction was carried out continuously for 6 hours, a solution that was continuously distilled out at a rate of 64.6 g/hr from the column top distillation port (T in FIG. 1) of the reactive distillation column was recovered and an analysis of the contents showed that methanol was 42.0% by weight, ethanol was 44.2% by weight, dimethyl carbonate was 8.2% by weight (12% by weight for the raw material feed amount), and ethyl methyl carbonate was 5.6% by weight (the reaction conversion rate of dimethyl carbonate: 88%). A solution that was continuously extracted out at a rate of 52.2 g/hr from the column bottom part (B in FIG. 1) of the reactive distillation column was recovered and an analysis of the contents showed that ethanol was 7.8% by weight, ethyl methyl carbonate was 2.9% by weight, diethyl carbonate was 88.8% by weight, and the others were 0.5% by weight (the reaction yield of diethyl carbonate: 78%).

Example 5

Production of Diethyl Carbonate

[Production Apparatus]

The reactive distillation column the same as in Example 1 was used.

[Reaction Method]

A raw material for production composed of dimethyl carbonate (DMC) and ethanol (EtOH) (mass ratio: EtOH (% by weight)/DMC (% by weight)=49.86/50.14) was continuously fed at a rate of 88.7 g/hr from the raw material introduction port (M in FIG. 1) between the 32th and 33th trays from the column top of the reactive distillation column.

Simultaneously, a sodium methoxide (MeONa) solution (mass ratio: MeONa (% by weight)/MeOH (% by weight)/EtOH (% by weight)=0.22/0.57/99.21) as a transesterification catalyst was also continuously fed at a rate of 25.1 g/hr from the catalyst introduction port (C in FIG. 1) between the 2nd and 3rd trays from the column top of the reactive distillation column.

At the above described feed rates, under reaction conditions of the reactive distillation column including under normal pressure, column top temperature of 69° C. to 73° C., column temperature of 73° C. to 78° C. (25th tray), column bottom temperature of 105° C. to 120° C., and reflux ratio: r of 2.8, reactive distillation was continuously carried out.

After the above described reaction was carried out continuously for 6 hours, a solution that was continuously distilled out at a rate of 68.7 g/hr from the column top distillation port (T in FIG. 1) of the reactive distillation column was recovered and an analysis of the contents showed that methanol was 36.1% by weight, ethanol was 48.1% by weight, dimethyl carbonate was 10.4% by weight (16% by weight for the raw material feed amount), ethyl methyl carbonate was 5.2% by weight, and the others were 0.2% by weight (the reaction conversion rate of dimethyl carbonate: 84%). A solution that was continuously extracted out at a rate of 45.1 g/hr from the column bottom part (B in FIG. 1) of the reactive distillation column was recovered and an analysis of the contents showed that ethanol was 1.4% by weight, ethyl methyl carbonate was 5.1% by weight, diethyl carbonate was 93.2% by weight, and the others were 0.3% by weight (the reaction yield of diethyl carbonate: 73%).

Comparative Example 1

Production of Diethyl Carbonate

[Production Apparatus]
The reactive distillation column the same as in Example 1 was used.

[Reaction Method]
A raw material for production composed of dimethyl carbonate (DMC) and ethanol (EtOH) (mass ratio: EtOH (% by weight)/DMC (% by weight)=51.57/48.43) was continuously fed at a rate of 88.0 g/hr from the raw material introduction port (M in FIG. 1) between the 32th and 33th trays from the column top of the reactive distillation column.

Simultaneously, a sodium methoxide (MeONa) solution (mass ratio: MeONa (% by weight)/MeOH (% by weight)/EtOH (% by weight)=0.85/2.18/96.97) as a transesterification catalyst was also continuously fed at a rate of 25.7 g/hr from the catalyst introduction port (C in FIG. 1) between the 2nd and 3rd trays from the column top of the reactive distillation column.

In the reactive distillation column, under reaction conditions including under normal pressure, column top temperature of 64° C. to 65° C., column temperature of 66° C. to 75° C. (25th tray), column bottom temperature of 80° C. to 100° C., and reflux ratio: r of 12, reactive distillation was continuously carried out.

After the above described reaction was carried out continuously for 6 hours, a solution that was continuously distilled out at a rate of 33.6 g/hr from the column top distillation port (T in FIG. 1) of the reactive distillation column was recovered and an analysis of the contents showed that methanol was 60.9% by weight, ethanol was 6.2% by weight, dimethyl carbonate was 32.7% by weight (25.8% by weight for the raw material feed amount), ethyl methyl carbonate was 0.1% by weight, and the others were 0.1% by weight (the reaction conversion rate of dimethyl carbonate: 74%). A solution that was continuously extracted out at a rate of 80.1 g/hr from the column bottom part (B in FIG. 1) of the reactive distillation column was recovered and an analysis of the contents showed that ethanol was 47.1% by weight, ethyl methyl carbonate was 4.7% by weight, diethyl carbonate was 46.2% by weight, and the others were 2.0% by weight (the reaction yield of diethyl carbonate: 66%).

A list of the test results of the above described Examples 1 to 5 and Comparative Example 1 is shown in Table 1.

TABLE 1

| | | Example 1 | Example 2 | Example 3 | Example 4 | Example 5 | Comparative Example 1 |
|---|---|---|---|---|---|---|---|
| Operation conditions | Multistage distillation column | Tray-type column | Tray-type column | Packing-type column | Tray-type column | Tray-type column | Tray-type column |
| | $\tau$ (h) | 0.22 | 0.14 | 0.11 | 0.08 | 0.22 | 0.11 |
| | [Cat] (mol · L$^{-1}$) | 0.026 | 0.016 | 0.011 | 0.015 | 0.004 | 0.007 |
| | $\tau \times$ [Cat] ($\times 10^3$) (h · mol · L$^{-1}$) | 5.7 | 2.4 | 1.2 | 1.1 | 0.8 | 0.7 |
| | Feed amount of dimethyl carbonate (mol · h$^{-1}$) | 0.5 | 0.5 | 0.5 | 0.5 | 0.5 | 0.5 |
| | Feed amount of ethanol/feed amount of dimethyl carbonate (mol/mol) | 3.1 | 3.1 | 3.1 | 3.1 | 3.0 | 3.0 |
| | Feed amount of a catalyst/feed amount of dimethyl carbonate ($\times 10^3$) (mol/mol) | 14 | 7.3 | 6.9 | 7.3 | 2.1 | 8.3 |
| | Reflux ratio | 2.7 | 2.1 | 3.2 | 2.4 | 2.8 | 12 |
| Operation results | Reaction conversion rate of dimethyl carbonate (%) | 97 | 94 | 92 | 88 | 84 | 74 |
| | Selectivity of diethyl carbonate (%) | 95 | 91 | 90 | 89 | 86 | 90 |
| | Reaction yield of diethyl carbonate (%) | 92 | 86 | 83 | 78 | 73 | 66 |

*1 $\tau$ represents the retention time (h) of DMC in the reaction space.
*2 [Cat] represents the catalyst concentration (mol · L$^{-1}$) in the reactive distillation column.

Example 6

Calculation of Reaction Rate Constant ($k_1$)

(6-1: EtOH/DMC=5 (mol); Measurement Temperature, 70° C., 50° C., and 30° C.)

In a 100 mL glass three-necked flask, 18 g of dimethyl carbonate (DMC; 0.2 mol) and 43 g of ethanol (EtOH; 0.93 mol) are mixed by stirring under a nitrogen atmosphere, and the temperature was increased to each measurement temperature (three points: 70° C., 50° C., and 30° C.). Then, 3 g of ethanol (0.07 mol) and 0.12 g of sodium methylate (500 ppm, 28% methanol solution) were added to start a reaction rate experiment (the time of end of addition was defined as 0 seconds of reaction time). After initiation of the reaction, this reaction solution was sampled appropriately, and the DMC consumption at each reaction time was calculated from gas chromatography measurement (internal standard method) to calculate the rate constant at each measurement temperature (three points).

(6-2: EtOH/DMC=1 (mol); Measurement Temperature, 15° C., 10° C., and 5° C.)

Next, a ratio of the use amount of EtOH to that of DMC is EtOH/DMC=1 (mol) and the use amount of sodium methylate is 1,000 ppm, an experiment was carried out in the same manner as in the above (6-1) to calculate the reaction rate constant at each reaction temperature (three points: 15° C., 10° C., and 5° C.)

(6-3: Calculation of Preexponential Factor A and Energy of Activation E)

When the results obtained from the above described (6-1) and (6-2) were calculated by using the equation (J), which is a general Arrhenius equation, A and E were as follows.

$$A = 2.66 \times 10^5$$

$$E = 4.16 \times 10^4$$

Example 7

Calculation of Apparent Reaction Rate Constant ($k_n$)

The apparent reaction rate constant: $k_{01}$ is represented by the equation (K). The apparent reaction rate constant: $k_{01}$ can be calculated from the equation (I) by using the Conv, τ, and [Cat] of the data shown in Table 1 of Examples (excluding Comparative Example 1). In the calculation of $k_{01}$, the volume of reaction solution per reaction stage (hold-up volume: $V_h$) was the actual measurement of the reactive distillation apparatus used in Example 1, and the volume of reaction solution in the reaction space in the reactive distillation column (hold-up volume: $V_H$) was $V_h \times$ the number of stages.

The $k_{01}$ was calculated so that the sum of square of the error between the actual value of the raw material DMC conversion rate: Conv and the calculated value of the DMC conversion rate was minimal by the least-squares method. The result is shown in FIG. 3.

Figure 3:
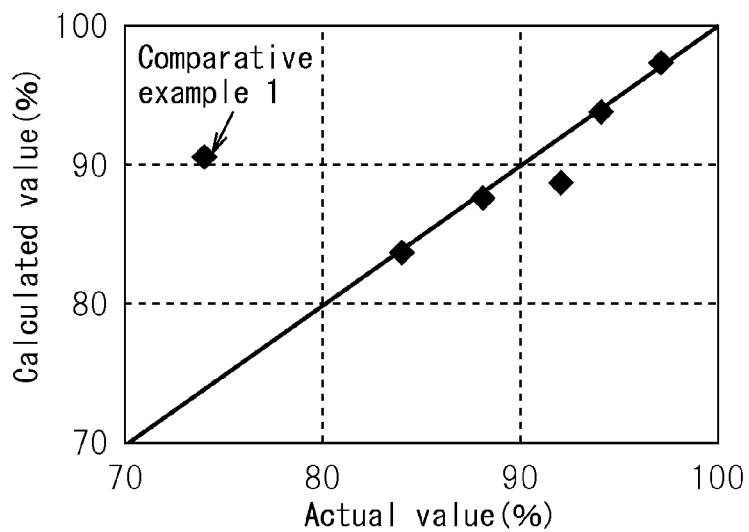
FIG. 3 is a graph showing the correlation between the data (actual value) shown in Table 1 in Examples and the calculated value (theoretical value).

From FIG. 3, the apparent reaction rate constant: $k_{01}$ (the slope of the line in FIG. 3) according to the Examples of the present invention was calculated as 6442 L·mol$^{-1}$·h$^{-1}$ (1.79 L·mol$^{-1}$·s$^{-1}$).

Reference Example 1

Calculation of Required Number of Reaction Stages

If the reaction in the present invention was, for example, supposed to be carried out under normal pressure and its reaction temperature was supposed to be 78° C., which is the boiling point of EtOH (under normal pressure), [EtOH]=10.38 mol·L$^{-1}$ was calculated from the equation (K) by using the $k_{01}$ calculated from the result of Example 7.

Therefore, from the inequality expression (S') or (W'), if the design (use) of the reactive distillation column, the feed volume and reflux ratio of raw materials to be used, and the objective reaction conversion rate of DMC are set, the required number of reaction stages: ΔN and the required reaction distance: ΔL in which DEC can be produced at a satisfactory yield can be calculated.

INDUSTRIAL APPLICABILITY

Diethyl carbonate obtained by the production method of the present invention is, for example, useful as dyes, intermediates of pigments, intermediates of agricultural chemicals, intermediates of pharmaceuticals, intermediates of organic materials in the electrical and electronic field, and solvents for synthesis of them, cleaners for printing, additives of soil modifying agents, and raw materials for producing of polycarbonate, and raw materials of battery electrolytes.

Diethyl carbonate obtained by the production method of the present invention, for example, has highly reduced contents of halogen ions or metal ions, other than the above described by-products, and is useful as intermediates of dyes or pigments, intermediates of agricultural chemicals, intermediates of pharmaceuticals, intermediates of organic materials in the electrical and electronic field, and solvents for synthesis of them, cleaners for printing, additives of soil modifying agents, and raw materials (monomers) for producing of polycarbonate, components of battery electrolytes, and the like.

REFERENCE SIGNS LIST

10 Reactive distillation column
12 Column top fraction recovery port
14 Catalyst introduction port
16 Raw material introduction port
18 Column bottom fraction recovery port
C Catalyst
M Raw material
T Column top fraction (low-boiling component)
B Column bottom fraction (high-boiling component)
RD Reaction distillation part
RC Concentrating part
RR Refluxing part
RH Spatial volume between raw material feed position and catalyst feed position
X Column top part
Y Upper column bottom
Z Lower column bottom
D1 Inner diameter of reaction distillation part
D2 Inner diameter of concentrating part
L1 Length of reaction distillation part
L2 Length of concentrating part
L3 Space between trays
N Nth stage of internals
n Number of stages of internals
ΔN Number of reaction stages

The invention claimed is:

1. A method of producing diethyl carbonate by reactive distillation comprising continuously feeding dimethyl carbonate and ethanol into a reactive distillation column to simultaneously carry out transesterification and distillation in the reactive distillation column in the presence of a transesterification catalyst, wherein
  (a) transesterification is in a countercurrent reaction mode in which a transesterification catalyst contacts dimethyl carbonate and ethanol;
  (b) a reactive distillation column is a multistage reactive distillation column having a column top part, a reaction distillation part having internals, and a concentrating part; and a side of the reaction distillation part is provided with a catalyst introduction port and a raw material introduction port located below the catalyst introduction port;
  (c) the transesterification catalyst is fed through the catalyst introduction port;
  (d) dimethyl carbonate and ethanol are fed through the raw material introduction port;
  (e) an amount of the transesterification catalyst used for 1 mol of dimethyl carbonate is 1 to 250 mmol;

(f) a ratio of the spatial volume between the catalyst introduction port and the raw material introduction port to a spatial volume of the reaction distillation part is 0.1 to 0.9;

(g) a reflux ratio of the reactive distillation column is 0.5 to 10; and (h) temperature in the column top part and the reaction distillation part is 60° C. to 100° C.

2. The method according to claim 1, wherein the internals are separated by perforated plate trays.

3. The method according to claim 2, wherein the number of stages of the reactive distillation column is 30 to 75.

4. The method according to claim 2, wherein a space between the raw material introduction port and the catalyst introduction port corresponds to 1 to 50 stages.

5. The method according to claim 1, wherein, in the reactive distillation column, a required number of reaction stages: $\Delta N$ defined as the number of stages between the catalyst introduction port and the raw material introduction port satisfies inequality expression (S):

$$\Delta N \geq \frac{v_0}{V_h} \times \frac{Conv}{3600 \times \exp(14.8311 - 5003.61/T) \times \frac{c}{B+rD} \times (1 - Conv)} \quad (S)$$

where $\Delta N$: Required number of reaction stages, $v_0$: Total feed volume of dimethyl carbonate, ethanol, and transesterification catalyst to the reactive distillation column per unit time (L·h$^{-1}$), $V_h$: Hold-up volume per reaction stage (L/number of stages), Conv: Reaction conversion rate of dimethyl carbonate, c: Feed amount of catalyst into reactive distillation column (mol·h$^{-1}$), B: Extraction volume from bottom of reactive distillation column (L·h$^{-1}$), r: Reflux ratio, D: Extraction volume from top of reactive distillation column (L·h$^{-1}$), and T: Column temperature (K).

6. The method according to claim 1, wherein, in the reactive distillation column, a required reaction distance: $\Delta L$ defined as a distance between the catalyst introduction port and the raw material introduction port satisfies inequality expression (W):

$$\Delta L \geq \frac{v_0}{d} \times \frac{Conv}{3600 \times \exp(14.8311 - 5003.61/T) \times \frac{c}{B+rD} \times (1 - Conv)} \quad (W)$$

where $\Delta L$: Required reaction distance (m), $v_0$: Total feed volume of dimethyl carbonate, ethanol, and transesterification catalyst to reactive distillation column per unit time (L·h$^{-1}$), d: Hold-up volume per meter in region between catalyst introduction port and raw material introduction port in reactive distillation column (L·m$^{-1}$), Conv: Reaction conversion rate of dimethyl carbonate, c: Feed amount of catalyst into reactive distillation column (mol·h$^{-1}$), B: Extraction volume from bottom of reactive distillation column (L·h$^{-1}$), r: Reflux ratio, D: Extraction volume from top of reactive distillation column (L·h$^{-1}$), and T: Column temperature (K).

7. The method according to claim 1, wherein pressure in the column top part and the concentrating part is normal pressure to 1,000 kPa.

8. The method according to claim 1, wherein the transesterification catalyst is at least one selected from the group consisting of an alkali metal hydroxide, an alkali metal carbonate compound, an alkali metal methoxide, and an alkali metal ethoxide.

9. The method according to claim 3, wherein a space between the raw material introduction port and the catalyst introduction port corresponds to 1 to 50 stages.

10. The method according to claim 2, wherein, in the reactive distillation column, a required number of reaction stages: $\Delta N$ defined as the number of stages between the catalyst introduction port and the raw material introduction port satisfies inequality expression (S):

$$\Delta N \geq \frac{v_0}{V_h} \times \frac{Conv}{3600 \times \exp(14.8311 - 5003.61/T) \times \frac{c}{B+rD} \times (1 - Conv)} \quad (S)$$

where $\Delta N$: Required number of reaction stages, $v_0$: Total feed volume of dimethyl carbonate, ethanol, and transesterification catalyst to the reactive distillation column per unit time (L·h$^{-1}$), $V_h$: Hold-up volume per reaction stage (L/number of stages), Conv: Reaction conversion rate of dimethyl carbonate, c: Feed amount of catalyst into reactive distillation column (mol·h$^{-1}$), B: Extraction volume from bottom of reactive distillation column (L·h$^{-1}$), r: Reflux ratio, D: Extraction volume from top of reactive distillation column (L·h$^{-1}$), and T: Column temperature (K).

11. The method according to claim 3, wherein, in the reactive distillation column, a required number of reaction stages: $\Delta N$ defined as the number of stages between the catalyst introduction port and the raw material introduction port satisfies inequality expression (S):

$$\Delta N \geq \frac{v_0}{V_h} \times \frac{Conv}{3600 \times \exp(14.8311 - 5003.61/T) \times \frac{c}{B+rD} \times (1 - Conv)} \quad (S)$$

where $\Delta N$: Required number of reaction stages, $v_0$: Total feed volume of dimethyl carbonate, ethanol, and transesterification catalyst to the reactive distillation column per unit time (L·h$^{-1}$), $V_h$: Hold-up volume per reaction stage (L/number of stages), Conv: Reaction conversion rate of dimethyl carbonate, c: Feed amount of catalyst into reactive distillation column (mol·h$^{-1}$), B: Extraction volume from bottom of reactive distillation column (L·h$^{-1}$), r: Reflux ratio, D: Extraction volume from top of reactive distillation column (L·h$^{-1}$), and T: Column temperature (K).

12. The method according to claim 4, wherein, in the reactive distillation column, a required number of reaction stages: ΔN defined as the number of stages between the catalyst introduction port and the raw material introduction port satisfies inequality expression (S):

$$\Delta N \geq \frac{v_0}{V_h} \times \frac{Conv}{3600 \times \exp(14.8311 - 5003.61/T) \times \frac{c}{B+rD} \times (1-Conv)} \quad (S)$$

where

ΔN: Required number of reaction stages, $v_0$: Total feed volume of dimethyl carbonate, ethanol, and transesterification catalyst to the reactive distillation column per unit time (L·h$^{-1}$), $V_h$: Hold-up volume per reaction stage (L/number of stages), Conv: Reaction conversion rate of dimethyl carbonate, c: Feed amount of catalyst into reactive distillation column (mol·h$^{-1}$), B: Extraction volume from bottom of reactive distillation column (L·h$^{-1}$), r: Reflux ratio, D: Extraction volume from top of reactive distillation column (L·h$^{-1}$), and T: Column temperature (K).

13. The method according to claim 2, wherein pressure in the column top part and the concentrating part is normal pressure to 1,000 kPa.

14. The method according to claim 3, wherein pressure in the column top part and the concentrating part is normal pressure to 1,000 kPa.

15. The method according to claim 4, wherein pressure in the column top part and the concentrating part is normal pressure to 1,000 kPa.

16. The method according to claim 5, wherein pressure in the column top part and the concentrating part is normal pressure to 1,000 kPa.

17. The method according to claim 6, wherein pressure in the column top part and the concentrating part is normal pressure to 1,000 kPa.

\* \* \* \* \*